United States Patent [19]
Bene et al.

[11] Patent Number: 5,470,483
[45] Date of Patent: Nov. 28, 1995

[54] DEVICE AND METHOD FOR CONTROLLING THE BALANCE OF FLUIDS IN AN EXTRACORPOREAL BLOOD CIRCUIT

[75] Inventors: Bernard Bene, Irigny; Nicolas Goux, Craponne, both of France

[73] Assignee: Hospal Industrie, France

[21] Appl. No.: 215,701

[22] Filed: Mar. 21, 1994

[30] Foreign Application Priority Data

Mar. 22, 1993 [FR] France ................................ 93 03468

[51] Int. Cl.[6] .......................... B01D 61/00; B01D 61/18; B01D 61/22; B01D 61/32
[52] U.S. Cl. .......................... 210/741; 210/85; 210/90; 210/97; 210/130; 210/134; 210/137; 210/254; 210/258; 210/321.65; 210/739; 210/645; 210/646; 210/650; 210/929; 604/4; 604/5; 604/6
[58] Field of Search .................... 210/645, 646, 210/650, 929, 741, 85, 90, 97, 130, 134, 137, 254, 258, 321.65, 321.72, 739; 604/4, 5, 6

[56] References Cited

U.S. PATENT DOCUMENTS

| | | | |
|---|---|---|---|
| 4,191,182 | 3/1980 | Popovich et al. | 210/929 |
| 4,204,957 | 5/1980 | Weickhardt | 210/929 |
| 4,711,715 | 12/1987 | Polaschegg | 210/137 |
| 4,713,171 | 12/1985 | Polaschegg | 210/110 |
| 4,894,164 | 1/1990 | Polaschegg | 210/646 |
| 4,964,976 | 10/1990 | Lysaght et al. | 210/650 |
| 5,178,763 | 1/1993 | Delaunay | 210/644 |
| 5,211,849 | 5/1993 | Kitaevich et al. | 210/645 |

FOREIGN PATENT DOCUMENTS

| | | |
|---|---|---|
| 0490212 | 6/1992 | European Pat. Off. . |
| 3620270 | 12/1987 | Germany . |
| WO79/01121 | 12/1979 | WIPO . |
| WO91/05576 | 5/1991 | WIPO . |

Primary Examiner—John Kim
Attorney, Agent, or Firm—Finnegan, Henderson, Farabow, Garrett & Dunner

[57] ABSTRACT

A device and method are provided for controlling the balance of fluids during an extracorporeal blood treatment session, according to which treatment, a certain quantity of liquid is withdrawn from the blood which is compensated for by the injection of a substitute liquid into the extracorporeal circuit. A recirculation circuit is provided and pressure is monitored. A pressure deviation within the recirculation circuit reflects a change in the balance between the quantity of liquid withdrawn from the blood and the quantity of liquid injected into the blood, and injection and/or withdrawal rates are altered to obtain a desired balance. The device and method are especially applicable to haemofiltration, haemodiafiltration and plasmapheresis.

12 Claims, 2 Drawing Sheets

5,470,483

DEVICE AND METHOD FOR CONTROLLING THE BALANCE OF FLUIDS IN AN EXTRACORPOREAL BLOOD CIRCUIT

BACKGROUND OF THE INVENTION

1. Field of the Invention

The present invention relates to the field of treatment of blood through extracorporeal circulation. More particularly, the invention concerns the treatment of blood where a certain quantity of liquid is extracted and is compensated for at least in part by the reinjection of a substitute liquid, as is done, for example with haemofiltration or haemodiafiltration.

2. Description of the Related Art

It is known to use a balance system to control equality between a quantity of liquid withdrawn from a patient and a quantity that is injected. For this purpose, the drawn-off liquid is collected in a bag, while the injected substitute liquid is taken from a bag. Each of the bags is hooked onto a balance. The reinjection flow rate of the substitute liquid is then controlled in accordance with the data supplied by the balance. Such a system, although reliable, has the disadvantage of being part of equipment that is expensive and difficult to operate.

If liquid withdrawn from a patient is set using a pump and the injection of a substitute liquid is also controlled by a pump, it is known that the balance between the quantity drawn off and the quantity of liquid injected can be controlled by setting the delivery rates of the pumps. This control, based on a flow meter, has the advantage of being simpler to operate and less expensive than control by weight analysis. However, a drawback with this system is that it is not completely reliable since a discrepancy may exist between the apparent delivery provided by a pump and its actual delivery.

SUMMARY OF THE INVENTION

An object of the invention is to mitigate these drawbacks and to provide a device and a method for controlling a balance of quantities of liquid injected into and withdrawn from the blood, which is reliable, inexpensive and simple to operate.

Another object of the invention is to provide a device and a control method that can be operated either during a blood treatment session or during maintenance operations.

To attain these various objects the present invention provides an apparatus used with a device for treating the blood of a patient including a first and a second line intended to be connected, on the one hand to a patient and, on the other hand, to the treatment element. The first line is intended for the blood flowing from the patient towards the treatment device, and the second line is intended for the blood flowing from the treatment device towards the patient. The apparatus further includes means capable of causing a certain quantity of liquid to be withdrawn from the blood, means for injecting into at least one of the lines, a quantity of the substitute liquid intended to compensate, at least partly, for the liquid that has been withdrawn. Also included is a bypass line for directly connecting the first line to the second line, as well as means for monitoring the course of the pressure inside a recirculation circuit constituted generally by the first line, the treatment element, the second line, and the bypass line.

The present invention also includes a method for controlling that the quantity of liquid withdrawn from the blood of a patient, circulating in an extracorporeal circulation circuit, is equal to the quantity of the substitute liquid injected for compensating the quantity extracted. The method includes the steps of creating a loop for the extracorporeal recirculation of the blood, which bypasses the patient, controlling in the course of time, the course of the pressure inside the recirculation loop, and modifying the extraction rate of the liquid and/or the reinjection rate to ensure that pressure corresponding to a correct compensation of the extracted liquid by the substitute liquid is maintained inside the reinjection loop.

Many advantages of the present invention will emerge from reading the description that follows with reference to the accompanying drawing figures which schematically illustrate various embodiments of the present invention, without any fixed scale.

BRIEF DESCRIPTION OF THE PREFERRED EMBODIMENTS

Figure 1:
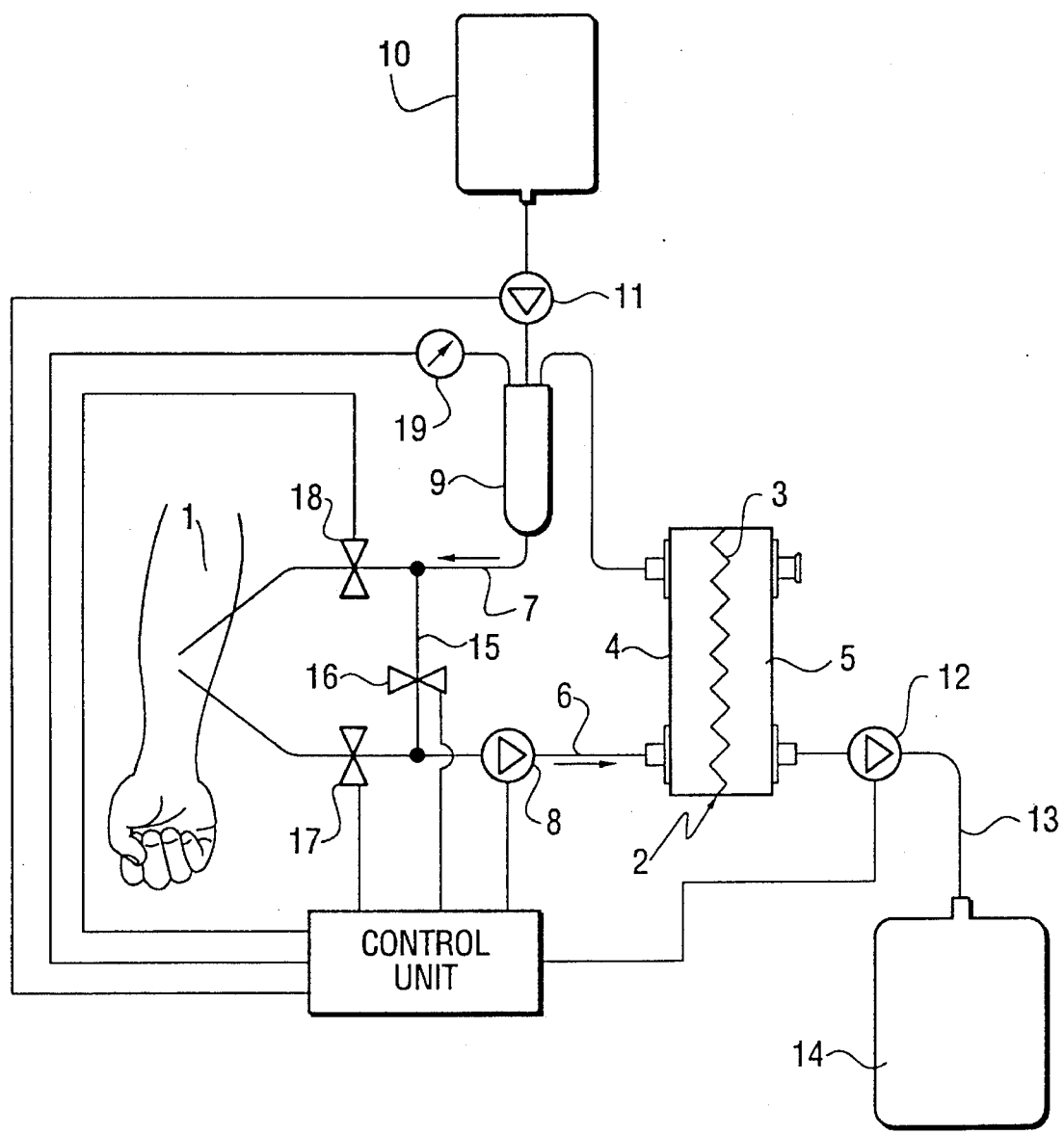
FIG. 1 illustrates a first embodiment of the present invention in relation to the technique of haemofiltration.

According to the embodiment of FIG. 1, the blood to be treated from a patient 1 is extracorporeally circulated in order to be treated by a treatment device such as exchanger 2. Exchanger 2 includes a membrane 3 that is suitable for ultrafiltration of blood. Membrane 3 divides the exchanger into two compartments—a first compartment 4 for receiving blood to be treated, and a second compartment 5 for receiving liquid withdrawn from the blood by ultrafiltration. The extracorporeal blood circuit includes an inlet line, such as arterial line 6, for the intake of blood to be treated from patient 1 to the exchanger 2, and an outlet line, such as venous line 7, for returning treated blood from the exchanger 2 to the patient 1. The blood is circulated by a pump 8 situated in the arterial line 6. The venous line 7 is provided with a bubble trap 9 also constituting a site for the injection of a substitute liquid that is present in a reservoir 10. The injection rate of the liquid is set by the delivery rate of the perfusion pump 11 located in line between reservoir 10 and bubble trap 9.

A fraction of the blood circulating in the first compartment 4 of the exchanger is ultrafiltrated across the membrane 3 by the action of a pump 12 situated in a line 13 connecting the second compartment 5 of the exchanger to a bag 14 for collecting the ultrafiltrate.

According to the invention, the extracorporeal blood circuit also includes a bypass line 15 directly connecting the arterial line 6 to the venous line 7. Bypass line 15 is provided with an obturating device, such as a clamp 16, and is connected to the arterial line at a point situated, relative to the direction of the blood flow, upstream from the pump 8 and very close to the patient 1. Similarly, bypass line 15 is connected to the venous line 7 downstream from the bubble trap 9 at a point very close to the patient 1.

The arterial line 6 (or the venous line 7, respectively) is also provided upstream (or downstream, respectively) from the point of intersection with the bypass line 15 with an obturating device such as a clamp 17 (or 18 respectively).

According to a characteristic of the invention, the bubble trap 9 is provided with a sensor 19 capable of indicating the pressure existing in the extracorporeal circuit.

The operation of the artificial kidney thus described is as follows. During the conventional operation in the haemofiltration mode, the clamp 16 is closed and the clamps 17 and 18 are opened. The pump 8 is controlled at the delivery rate desired for the circulation of blood inside the extracorporeal circuit. The extraction pump 12 is operated for producing low pressure in the compartment 5 of the exchanger and, therefore, blood ultrafiltration occurs across the membrane 3. The ultrafiltration rate of the blood corresponds to the delivery rate of the pump 12. After having passed into the exchanger, the blood is restored to the patient via the venous line 7. In order to compensate wholly or partially for the loss of liquid that occurs as the result of ultrafiltration, a substitute liquid is added to the blood before its return to the patient. This addition is obtained by injecting into the bubble trap 9, a liquid coming from the reservoir 10. The injection rate of the liquid is set by the delivery rate of the injection pump 11. When it is not necessary to produce a loss of weight in the patient, the delivery rate of the injection pump 11 is controlled so that it should be equal to the delivery rate of the extraction pump 12. Thus the whole volume of liquid extracted from the blood by ultrafiltration is compensated for by the injection of an identical volume of substitute liquid.

According to the invention, the check that this compensation is exact is effected as follows. The clamp 16 is opened and the clamps 17 and 18 are closed simultaneously. The patient is thus isolated from the extracorporeal circuit while operation of pumps 8, 11 and 12 is maintained. The blood then recirculates inside a closed loop constituted by the arterial line 6, the compartment 4 of the exchanger, the venous line 7 and the bypass line 15. Pressure inside the extracorporeal circuit can be monitored with the sensor 19, that may be connected to a graphic recording device (not shown), or to a device for processing the signal such as control unit 30. When the extraction rate of the pump 12 is exactly equal to the injection rate of the pump 11, the pressure value indicated by the sensor 19 remains constant, or at least substantially constant. Indeed, it is possible to note pressure variations due to sudden surges of the pumps, the average value of the pressure being kept constant. On the other hand, when the delivery rates of the pumps are supposed to be equal and one nevertheless notes a pressure variation, this means that the actual delivery rate provided by at least one of the pumps is not equal to the set point delivery. Thus, if the pressure indicated by the sensor 19 increases, this means that the injection rate is less than the extraction rate. It is then possible to correct one or the other of the pumps for obtaining a real compensation of the quantity of the ultrafiltrated liquid by an equal quantity of the substituted liquid.

Moreover, according to the invention, a calibration of one of the pumps relative to the other may be effected. Indeed, it is possible to identify the value of each of the set points or displayed deliveries of the pumps 11 or 12, which makes it possible to obtain pressure stability and hence a real compensation. For example, it may happen that because of intrinsic errors in each of the pumps, the ultrafiltration produced by the operation of the extraction pump 12 at a displayed delivery rate of 100 ml/min would only be actually compensated by an injection of liquid by means of the injection pump 11 having a displayed delivery rate of 102 ml/min and not 100 ml/min.

This ratio of the displayed or set point delivery rates may be kept in the memory (not shown) and may subsequently be used for correcting the set point value of the delivery rates if a real compensation of the ultrafiltrated liquid by the substitute liquid is desired.

Figure 2:
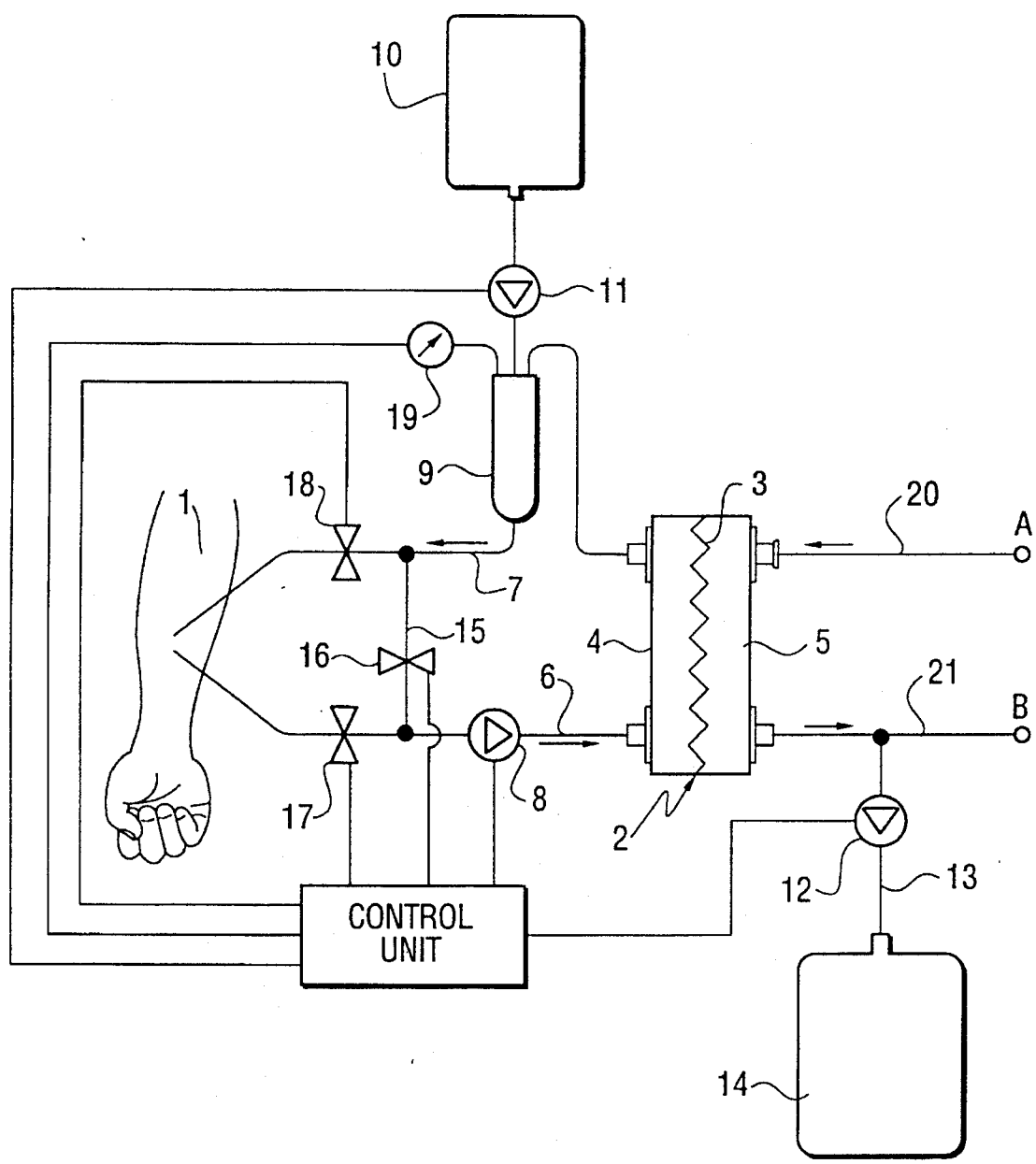
FIG. 2 illustrates a second embodiment of the present invention in relation to the technique of haemodiafiltration.

According to the embodiment of FIG. 2, wherein the elements that are identical with those of FIG. 1 are indicated by the same reference numerals, the compartment 5 of the exchanger 2 is traversed by a dialysis liquid. A line 20 directs dialysis liquid from a source (not shown) towards the compartment 5, while a line 21 directs dialysis liquid from the compartment 5 to evacuation or regeneration means. The liquid flowing in the line 21 contains impurities from the blood due to the diffusion effect. Specifically, concentration differences on either side of the membrane 3 result in blood impurities being passed through the membrane 3.

Moreover, the dialysis liquid volume is increased at the outlet of the compartment 5 by a volume of liquid ultrafiltrated from the blood by a convection effect. This convection effect is due to a difference in pressure on either side of the membrane. Thus, in FIG. 2, if the flow rate at point A of the dialysis liquid line 20 is kept equal to the flow rate of liquid at point B of the line 21, the ultrafiltration is produced by the low pressure created by the extraction pump 12 situated in the line 13 in which flow rate is equal to the ultrafiltration flow rate. In a manner similar to the embodiment described above, the quantity of liquid extracted from the blood by ultrafiltration is compensated for by an equal quantity of substitute liquid injected by the injection pump 11, the set point delivery rate of which is the same as that of the extraction pump 12. The technique here used for the purification of the blood is haemofiltration.

According to the invention, to check the exactness of the actual compensation between the ultrafiltrated liquid and the injected liquid in the second embodiment of the invention, one proceeds in a manner similar to the manner described in connection with the embodiment of FIG. 1. The clamp 16 is opened while the clamps 17 and 18 are simultaneously closed to isolate the patient 1 and thus to create a loop for the recirculation of the blood within the extracorporeal circuit. An indication by the sensor 19 that the pressure has been maintained at a substantially constant value is proof of perfect compensation. It is then possible to proceed in the same way as in the preceding embodiment with the relative calibration of one of the pumps in relation to the other.

According to the mode here described, the dialysis liquid circuit is an open circuit, with a line 20 for the intake of dialysis liquid and a line 21 for the return of dialysis liquid. The present invention may also be used where the dialysis liquid circuit has a closed portion, including the compartment 5 of the exchanger, to which the line 13 is connected for extracting a quantity of liquid equal to the quantity of liquid extracted from the blood by ultrafiltration.

The operation of the cycle for checking whether the compensation between the flow rate of the ultrafiltrated liquid and the injected substitute liquid is exact may be effected in an automated manner according to a predetermined frequency during the treatment of the blood. In this case, the command for opening and closing the valves may be effected by a control unit 30. Similarly, the data transmitted by the sensor 19 may be recorded and processed by the control unit 30. The frequency and the duration of the checking cycle must be chosen so as not to impair the efficiency of the whole of the blood treatment session. However, the present invention makes it possible to detect very quickly a deviation from the balance of liquid extracted from the blood and the quantity of the liquid reinjected into the blood. Indeed, during tests carried out with an ultrafiltration and injection flow rate of 1.8 1/h, it has been possible to obtain in one minute a visual appreciation on a graphic recording device with a deviation of 50 ml/h.

The present invention has been described for cases where the set point flow rate of the extraction pump 12 and the injection pump 11 are equal. If it is desired to obtain a loss of weight in the patient, and where an extraction rate is, therefore, set higher than the injection rate, it is possible to determine the desired course of the pressure within the recirculation loop for a given difference in the flow rate from the characteristics of the circuit and of the exchanger 2. A determination that the flow rates provided are accurate is accomplished by observing the actual course of the pressure and then by comparing it with a desired pressure course.

Alternatively, even if the treatment of blood is effected under delivery conditions that are different for the extraction pump and the injection pump, it is possible, during the operation of the checking process in accordance with the invention, to temporarily create an equality of the flow rate. Thus, the two pumps can be calibrated relative to each other, and the treatment session can continue by taking into account the data obtained during the calibration for the set point delivery rate.

The present invention has the particular advantage of using a physical value (pressure) different in kind from those that one wishes to check (flow rate, weight) in order to control fluid balance. This advantage may lead to integrating this control process into the safety system of the treatment device.

The present invention also finds an application outside the blood treatment sessions during the operations of maintenance and checking of the dialysis apparatuses. In this case, the liquid circulating in the extracorporeal blood circuit is not blood, but the calibration relating to the extraction pump relative to the injection pump may be effected in a simple and reliable manner.

The present invention also finds an application in the operations of treating blood by plasmapheresis, where the plasma extracted from the blood is replaced by a substitute liquid.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A blood treatment apparatus, comprising:
    a treatment device;
    an inlet line connected to the treatment device for conveying blood from the vascular system of a patient into the treatment device;
    an outlet line connected to the treatment device for conveying blood away from the treatment device back to the patient;
    a bypass line interconnecting the inlet line and the outlet line; the inlet line, the outlet line, and the bypass line defining a recirculation loop;
    means for selectively preventing flow between the recirculation loop and the patient to isolate the patient therefrom;
    means connected to one of said inlet line and said outlet line for injecting a substitute liquid into the recirculation loop;
    means connected to the treatment device for withdrawing liquid from blood in the treatment device; and
    pressure measuring means connected to the recirculation loop for generating a signal indicative of a difference between a flow rate of the substitute liquid and a flow rate of the liquid withdrawn from blood in the treatment device when the recirculation loop is isolated from the patient.

2. An apparatus according to claim 1 wherein the injecting means includes an adjustable delivery rate pump.

3. An apparatus according to claim 1 wherein the withdrawing means includes an adjustable delivery rate pump.

4. An apparatus according to claim 1 wherein the treatment device is a dual compartment ultrafiltration exchanger having first and second compartments separated by a membrane, the first compartment configured for receiving liquid removed from the blood by ultrafiltration.

5. An apparatus according to claim 4 wherein the second compartment is also configured for circulation of dialysis liquid, the apparatus further including a dialysis liquid intake line connected to the second compartment and a dialysis liquid evacuation line connected to the second compartment.

6. An apparatus according to claim 1, further including means for regulating at least one of the injecting means and the withdrawing means in response to the signal generated by the pressure measuring means.

7. An apparatus according to claim 6 wherein the regulating means includes a control unit connected to the pressure measuring means, the injecting means, and the withdrawing means.

8. An apparatus according to claim 1, further including means for calibrating one of the injecting means and the withdrawing means in relation to another of the injecting means and the withdrawing means, from the signal generated by the pressure measuring means.

9. An apparatus according to claim 8 wherein the calibrating means includes a control unit connected to the pressure measuring means, the injecting means, and the withdrawing means.

10. A method for controlling liquid injection and withdrawal from an extracorporeal blood circuit connected to a vascular system of a patient so that equal quantities of liquid are injected and withdrawn from the circuit, the method comprising the steps of:
    isolating a recirculation loop from the patient, the loop including a blood inlet line, a blood treatment device, a blood outlet line, and a bypass line connecting the blood inlet line to the blood outlet line;
    circulating blood through the loop;
    monitoring the pressure in the loop over a period of time; and
    modifying one of an injection rate of liquid into the loop and a withdrawal rate of liquid from the loop in order to obtain a substantially constant pressure when a nonconstant pressure is detected over a period of time during the step of monitoring.

11. A method according to claim 10 further comprising the step of establishing a correlation between an apparent withdrawal delivery rate and an apparent injection delivery rate.

12. A method according to claim 11 wherein the extracorporeal blood circuit is a haemofiltration circuit.

* * * * *